(12) United States Patent
Leroy et al.

(10) Patent No.: US 7,955,292 B2
(45) Date of Patent: Jun. 7, 2011

(54) ENDOSURGICAL EXTRACTION BAG FOR COLLECTING BODY TISSUE OR BODY FLUID

(75) Inventors: Joel Jules Louis Leroy, Bully les Mines (FR); Jacques Francois Bernard Marescaux, Scharrachbergheim (FR); Didier Raoul Daniel Mutter, Vendenheim (FR); Michel Joseph Emile Vix, Niederhausbergen (FR)

(73) Assignee: MTP Medical Technical Promotion GmbH (DE)

( * ) Notice: Subject to any disclaimer, the term of this patent is extended or adjusted under 35 U.S.C. 154(b) by 0 days.

(21) Appl. No.: 11/627,859

(22) Filed: Jan. 26, 2007

(65) Prior Publication Data

US 2007/0179458 A1    Aug. 2, 2007

Related U.S. Application Data

(63) Continuation of application No. PCT/EP2005/008052, filed on Jul. 23, 2005.

(30) Foreign Application Priority Data

Jul. 28, 2004    (DE) .......................... 10 2004 038 071

(51) Int. Cl.
| | |
|---|---|
| A61F 13/20 | (2006.01) |
| A61M 31/00 | (2006.01) |
| A61M 1/00 | (2006.01) |
| A61B 1/00 | (2006.01) |
| A61B 1/32 | (2006.01) |
| B65D 30/22 | (2006.01) |
| B65D 33/00 | (2006.01) |
| B65D 65/26 | (2006.01) |
| B65D 77/00 | (2006.01) |
| A61B 17/00 | (2006.01) |
| B65D 79/00 | (2006.01) |

(52) U.S. Cl. .............. 604/13; 604/27; 604/48; 604/327; 600/204; 600/104; 600/114; 600/121; 600/139; 383/210.1; 383/38; 383/105; 383/127; 206/216; 206/438; 206/527

(58) Field of Classification Search .................. 604/403, 604/408–410; 220/62.22; 383/210.1; 600/573
See application file for complete search history.

(56) References Cited

U.S. PATENT DOCUMENTS 3,780,739 A * 12/1973 Frank ........................... 604/335
(Continued)

FOREIGN PATENT DOCUMENTS

CA    20986630    3/2005
(Continued)

OTHER PUBLICATIONS

International Preliminary Report on Patentability, Jan. 30, 2007, 8 pages.

(Continued)

*Primary Examiner* — Leslie R Deak
*Assistant Examiner* — Adam Marcetich
(74) *Attorney, Agent, or Firm* — St. Onge Steward Johnston & Reens LLC

(57) ABSTRACT

The invention relates to an endosurgical extraction bag for collecting body tissue or body fluid, with a bag main part formed from a flexible envelope, and with a first admission opening for introducing tissue or fluid into the bag main part of the bag. Arranged in the bag main part, there is an inner envelope which is connected to the main part (bag) and opens toward the first admission opening, but adjoins the bag main part sealingly in respect of the first admission opening, and which has a second admission opening at its second end remote from the first admission opening and spaced apart from an end of the bag main part remote from the first admission opening, through which second admission opening the tissue or fluid can be introduced into the bag main part.

9 Claims, 6 Drawing Sheets

U.S. PATENT DOCUMENTS

| | | | |
|---|---|---|---|
| 5,037,379 A * | 8/1991 | Clayman et al. | 600/37 |
| 5,143,082 A * | 9/1992 | Kindberg et al. | 600/562 |
| 5,215,521 A * | 6/1993 | Cochran et al. | 604/22 |
| 5,234,439 A * | 8/1993 | Wilk et al. | 606/114 |
| 5,312,416 A * | 5/1994 | Spaeth et al. | 606/114 |
| 5,341,815 A * | 8/1994 | Cofone et al. | 600/562 |
| 5,352,184 A * | 10/1994 | Goldberg et al. | 600/37 |
| 5,354,132 A * | 10/1994 | Young et al. | 383/49 |
| 5,354,303 A * | 10/1994 | Spaeth et al. | 606/128 |
| 5,368,545 A | 11/1994 | Schaller et al. | 600/37 |
| 5,374,273 A * | 12/1994 | Nakao et al. | 606/127 |
| 5,480,404 A * | 1/1996 | Kammerer et al. | 606/113 |
| 5,681,324 A | 10/1997 | Kammerer et al. | 606/113 |
| 5,785,677 A * | 7/1998 | Auweiler | 604/28 |
| 5,788,709 A * | 8/1998 | Riek et al. | 606/114 |
| 5,836,936 A | 11/1998 | Cuschieri | 606/1 |
| 5,846,251 A * | 12/1998 | Hart | 606/127 |
| 6,206,889 B1 * | 3/2001 | Bennardo | 606/127 |
| 6,228,095 B1 * | 5/2001 | Dennis | 606/114 |
| 6,406,440 B1 * | 6/2002 | Stefanchik | 600/562 |
| 7,041,055 B2 * | 5/2006 | Young et al. | 600/204 |
| 2003/0139767 A1 * | 7/2003 | Jespersen | 606/205 |

FOREIGN PATENT DOCUMENTS

| | | |
|---|---|---|
| DE | 92 08 489 | 9/1992 |
| DE | 92 12 714 | 12/1992 |
| DE | 41 40 156 | 6/1993 |
| DE | 42 42 153 | 6/1994 |
| DE | 43 18 098 | 9/1994 |
| DE | 43 37 182 | 5/1995 |
| DE | 196 24 826 | 1/1998 |
| EP | 0 578 997 | 1/1994 |
| EP | 0 696 899 | 2/1996 |
| EP | 0 947 166 | 10/1999 |
| EP | 1 132 051 | 9/2001 |
| WO | 93/15675 | 8/1993 |

OTHER PUBLICATIONS

International Search Report/Written Opinion, Nov. 2, 2005, 4 pages.

* cited by examiner

ENDOSURGICAL EXTRACTION BAG FOR COLLECTING BODY TISSUE OR BODY FLUID

CROSS REFERENCE TO RELATED APPLICATIONS

The present application is a continuation of pending International patent application PCT/EP 2005/008052 filed on Jul. 23, 2005 which designates the United States and claims priority of German patent application No. 10 2004 038 071.6 filed on Jul. 28, 2004.

BACKGROUND OF THE INVENTION

The invention relates to an endosurgical extraction bag for collecting body tissue or body fluid, comprising a bag main part formed from a flexible envelope, and a first admission opening for introducing tissue or fluid into the bag main part.

The invention also relates to an applicator for introducing an extraction bag into the body through a natural or artificial opening in the body.

Such an extraction bag, also referred to as a laparoscopy bag, is used to remove tissue or also body fluid from the human or animal body.

An endosurgical extraction bag of this kind is used in particular in endoscopic interventions in the human body that are performed through a small artificially created or natural opening. For example, when removing tumor tissue from the abdominal space, it is important that, when removing the tumor tissue, the latter does not come into contact with healthy or uninvolved tissue, so as in this way to avoid metastasis and thus avoid harming the patient. If tumor tissue or tissue parts have to be removed, they are therefore introduced into an extraction bag at the site where they have been detached from the surrounding tissue, after which the extraction bag is withdrawn from the body, normally through a trocar. The extraction bag is accordingly brought into position in the body, normally through a trocar, before introduction of the tissue into the extraction bag.

An important requirement of such an extraction bag is that the tissue collected in the extraction bag cannot escape before the extraction bag is withdrawn from the body. For this reason, extraction bags have been produced, particularly such as the one described in the document EP 0 578 997 B1, which have drawstrings for closing the admission opening through which the tissue is introduced into the extraction bag. Despite a closure possibility of this kind, reliable sealing of the extraction bag is not guaranteed in every case.

Another extraction bag is known from the document EP 0 696 899 B1, This extraction bag comprises a bag with two openings, namely one small opening and one larger opening. Seen in the longitudinal direction of the extraction bag, the openings are each located at a respective end of the extraction bag. Provision of two openings lying opposite one another is intended to allow a gripping instrument to be guided through the smaller opening in order to be able to comminute tissue that has been introduced through the large opening in the bag. For both openings, drawstrings are once again provided for closing the openings, which, as in the known extraction bag described above, entails the disadvantage of inadequate sealing.

A further disadvantage of the known extraction bags is that they are unnecessarily large, especially for their use in pathology, since only small pieces of tissue are removed for pathology purposes and then examined after removal from the body.

SUMMARY OF THE INVENTION

It is an object of the invention to make available an extraction bag of the type mentioned in the introduction, in which body tissue or body fluid can be introduced as safely as possible against escape, so that the content can be safely removed from the body upon withdrawal of the extraction bag.

A further object of the invention is to make available an applicator with which an extraction bag, in particular an extraction bag according to the invention, can be introduced into position in the body in a simple and reliable manner.

According to an aspect of the invention, an endosurgical extraction bag for collecting body tissue or body fluid is provided, comprising a bag main part formed from a flexible envelope, an inner envelope arranged in the bag main part, the inner envelope having a first end connected to the bag main part and forming a first admission opening, but adjoining the bag main part sealingly in respect of the first admission opening, and a second end remote from the first admission opening and spaced apart from an end of the bag main part remote from the first admissing opening which forms a second admission opening through which the tissue of fluid can be introduced into the bag main part.

The extraction bag according to the invention therefore comprises a bag main part and an inner envelope arranged in the latter. The inner envelope has two open ends, one open end forming the first admission opening, so that tissue or fluid can be guided first through this opening into the inner envelope, and this tissue can then be introduced into the bag main part via the second admission opening at the second end of the inner envelope. The inner envelope arranged in the bag main part acts with its second end as a kind of valve, the operating principle of which corresponds to that of a fish trap. Tissue or fluid can accordingly be introduced through the inner envelope and through the latter's second end into the bag main part or into that portion of the bag main part that is not occupied by the inner envelope and thus constitutes a reservoir for the tissue or the fluid. Conversely, however, the tissue located in the bag main part or reservoir cannot, without outside intervention, pass back through the second admission opening into the interior of the inner envelope and thus escape from the extraction bag as a whole. In this way, a very high level of sealing of the extraction bag is already achieved even without additional closure means for the first admission opening, such as drawstrings or the like. Since it is possible in principle to dispense with drawstrings or the like for closing the admission opening of the bag main part, the handling of the extraction bag according to the invention is also considerably simplified compared to that of the known extraction bags, because the additional step of closing the first or second admission opening of the known extraction bags can be omitted, and especially as this step in the known extraction bags has to be performed inside the body and is therefore difficult.

In a preferred embodiment, the space between the outer face of the inner envelope and the inner face of the envelope of the bag main part serves as a reservoir for the body tissue or body fluid.

An advantage of this measure is that the body tissue or body fluid can be introduced into the space between the outer face of the inner envelope and the inner face of the envelope of the bag main part and, as a consequence, escape of the tissue or fluid can be even more safely avoided, because the tissue is trapped in this reservoir.

In another preferred embodiment, the inner envelope has a funnel-shaped configuration.

This measure has the advantage that introduction of tissue through the inner envelope into the bag main part is simplified, because the tip of the instrument, with which the tissue is gripped, is as it were forcibly guided by the funnel-shaped configuration of the inner envelope into the bag main part or reservoir.

In this connection, it is preferable if the second end (inner end) of the inner envelope, transverse to the longitudinal direction, is narrower than the bag main part at this second end.

By means of this measure, the valve function of the inner envelope is still further improved, and, in particular, the danger of a tissue piece already introduced into the bag main part or reservoir passing back into the inner envelope and of tissue escaping from the extraction bag is reduced, because the cross section of the second admission opening is smaller than the cross section of the bag main part.

In another preferred embodiment, the second end of the inner envelope is spaced apart from the first admission opening by a distance which is in the region of approximately one quarter to approximately three quarters of the distance of the first admission opening from that end of the bag main part lying remote from the first admission opening.

By virtue of this configuration, the inner envelope thus basically extends from the first admission opening to a middle area of the interior of the bag main part, and without reaching the opposite end of the bag main part, such that, on the one hand, it is possible to ensure that the tissue to be introduced passes completely through the second admission opening of the inner envelope and does not partially still lie inside the inner envelope when the instrument has been withdrawn again from the extraction bag. On the other hand, it is ensured that the tissue has to be introduced as deep as possible into the interior of the extraction bag, thus eliminating or at least minimizing the danger of incorrect handling of the extraction bag. In addition, the fish trap function of the inner envelope is further improved by this measure.

In another preferred embodiment, the inner envelope is connected to the envelope of the bag main part only in its area directed toward the first admission opening.

According to this embodiment, therefore, the inner envelope is substantially loose in relation to the envelope of the bag main part, such that a tissue sample can reach in particular between the outer face of the inner envelope and the inner face of the envelope of the bag main part, by which means an escape of the tissue sample from the bag main part can be still more reliably avoided. It will be appreciated here that the area of the inner envelope directed toward the first admission opening is connected to the envelope of the bag main part tightly, in particular in a liquid-tight manner, about the entire periphery.

In another preferred embodiment, the inner envelope is connected integrally to the envelope of the bag main part.

This measure is advantageous in the production of the extraction bag, since the inner envelope does not have to be connected to the envelope of the bag main part by a joining technique such as welding or adhesive bonding.

In another preferred embodiment, the inner envelope is formed by turning inward of a section of the envelope of the bag main part.

This measure has the particular advantage that the production of the extraction bag according to the invention, with bag main part and inner envelope, is very simple and therefore particularly cost-effective.

In another preferred embodiment, the first admission opening can be closed.

As has already been mentioned above, closure means for closing the first admission opening are normally not needed, because of the inventive configuration of the extraction bag and the fish trap function of the inner envelope, but they may nonetheless be provided, for example, for special applications, in particular for fluids.

The closable nature of the admission opening is also not so much intended for preventing escape of tissue during withdrawal of the extraction bag from the body, but may be advantageous, for example, if the extraction bag with the tissue contained in it has to be stored for a certain period of time, thus avoiding penetration of contaminants into the interior of the inner envelope and thus into the bag main part, and likewise avoiding contamination of the (healthy) body tissue by tissue pieces that are located in the bag main part (reservoir) of the extraction bag.

For easier manipulation of the extraction bag in the inside of the body, means are preferably provided for gripping the extraction bag with an instrument, for example gripping forceps, the means for gripping preferably comprising a thread, a thread loop, or an eyelet in the envelope, in which case, however, the aforementioned eyelet is then arranged at a location of the envelope of the bag main part that does not impair the tightness of the bag main part.

For this purpose, if appropriate, an additional sealing connection of the inner envelope and of the bag main part is to be provided on that side of the eyelet which is remote from the first admission opening of the extraction bag.

In another preferred embodiment, the envelope of the bag main part and/or the inner envelope is formed from two foils lying substantially flat on one another.

The advantage of this is that the extraction bag as a whole has a very small thickness and, in particular, can be rolled up into a roll with small diameter, thus making it easier to introduce the extraction bag into the body. Moreover, in respect of the inner envelope, this measure has the further advantage that the second admission opening is designed as a very narrow gap which can be easily widened out when tissue is introduced by means of an instrument, but which automatically forms a very narrow gap again once the instrument has been withdrawn from the inner envelope, as a result of which the valve function of the inner envelope, in the manner of a fish trap, is still further improved.

In another preferred embodiment, the extraction bag is designed such that it can be rolled up and, from the rolled-up state, converts more or less independently into an unrolled flat state.

This has the advantage of simplifying the handling of the extraction bag during introduction into the body, because the extraction bag can be easily introduced in the rolled-up state for example through a trocar or through an applicator according to the invention, which applicator is described below, and, after emerging from the trocar or applicator inside the body, it unrolls independently, without awkward maneuvers being required in order to do this.

According to another aspect of the invention, an applicator for introducing an extraction bag, in particular an extraction bag according to one of the aforementioned embodiments, into the body through a natural or artificial opening in the body is provided, comprising a tube into which the extraction bag can be inserted in a rolled-up state, and a ram insertable into the tube and movable in a longitudinal direction of the tube in order to push the extraction bag out of the tube.

The ram is preferably movable in the tube by pushing, but can also be movable in the tube by means of a screw thread.

The length of the tube is preferably adapted such that at least two extraction bags can be received one behind the other in the tube.

The advantage of this is that at least two extraction bags can be introduced at the same time into the body without removing the tube from the body, as a result of which the introduction of several extraction bags is possible with minimal time expenditure.

The tube can be introduced into the body through a trocar.

Further advantages and features will become evident from the following description and from the attached drawing.

It will be appreciated that the aforementioned features and those still to be explained below can be used not only in the respectively cited combination but also in other combinations or singly, without departing from the scope of the present invention.

BRIEF DESCRIPTION OF THE DRAWINGS

Illustrative embodiments of the invention are depicted in the drawing and are described in more detail below with reference to this drawing, in which.

DETAILED DESCRIPTION OF PREFERRED EMBODIMENTS

Figure 1:
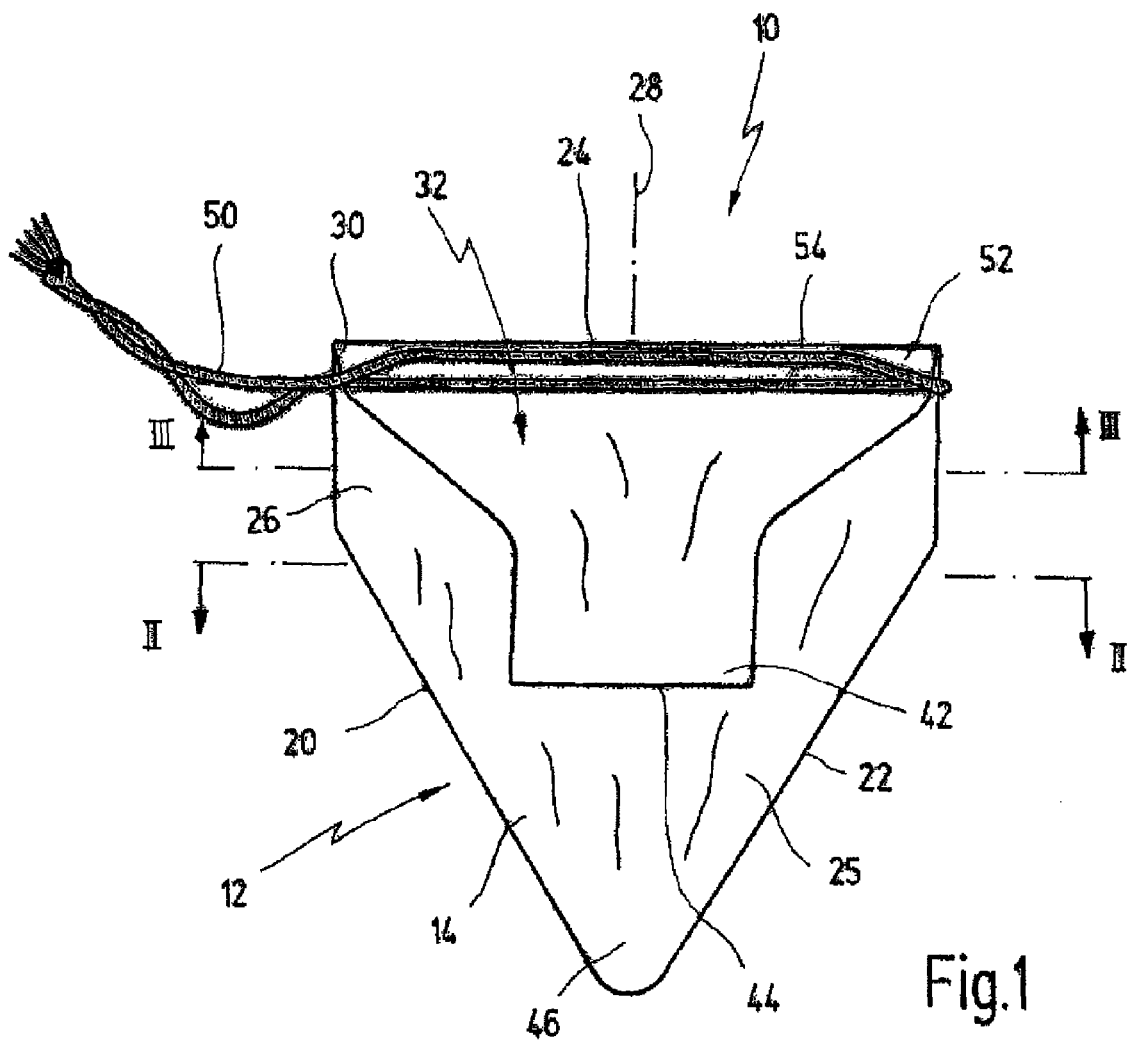
FIG. 1 shows an endosurgical extraction bag in a side view.
Figure 2:
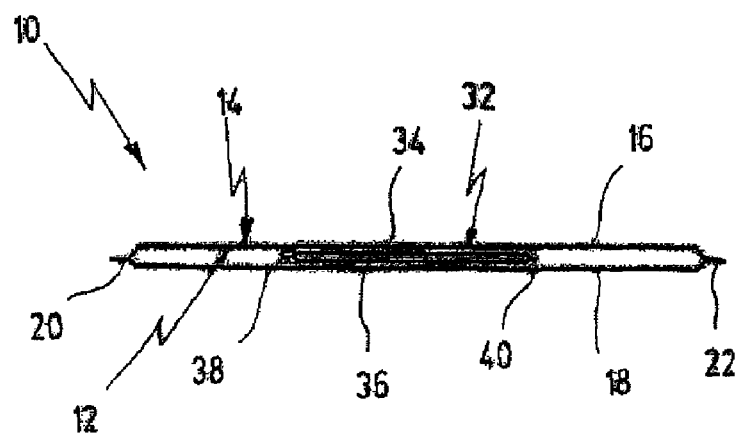
FIG. 2 shows a section through the extraction bag along the line II-II in FIG. 1.
Figure 3:
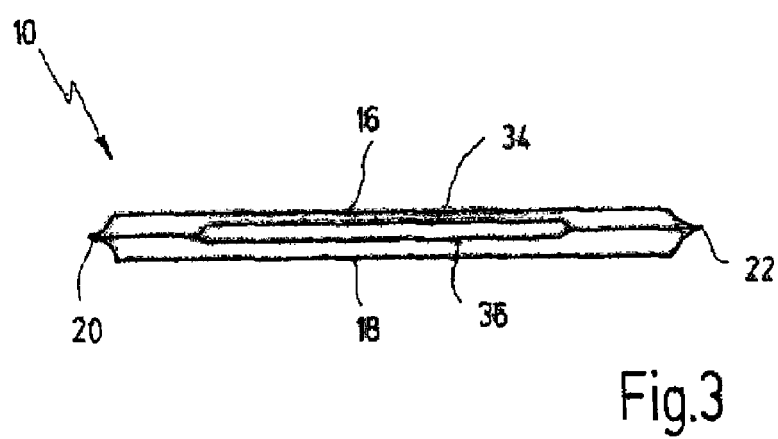
FIG. 3 shows a section through the extraction bag along the line III-III in FIG. 1.

In FIGS. 1 to 3, an endosurgical extraction bag for collecting body tissue or body fluid is indicated by the general reference number 10. The extraction bag 10 is used principally for pathology purposes. Tissue introduced into the extraction bag 10 inside the body can be removed from the body with the extraction bag 10 and then examined for pathology.

The extraction bag 10 comprises a bag main part 12 formed from a flexible envelope 14. The envelope 14 is transparent and is made, for example, of polymethylene or polymethane.

The envelope 14 is formed from two foils 16 and 18 which lie flat on one another and are fixedly connected to one another at their lateral edges 20 and 22, preferably by welding or heat-sealing.

A substantially triangular section 25 of the bag main part 12 is adjoined by a substantially rectangular section 26 of the bag main part 12.

The extraction bag 10 also has a first admission opening 24 through which tissue or fluid can be introduced into the bag main part 12 g, as will be described later, without the interior of the bag main part 12 or of a reservoir 12, which is described later, being open to the outside of the extraction bag 10 at the first admission opening 24; instead the bag main part 12 is also closed tight at the admission opening 24.

The first admission opening 24 extends, transversely with respect to a longitudinal axis or longitudinal direction 28 of the extraction bag 10, across the full width of the extraction bag 10. The admission opening 24 is located at one end 30 of the extraction bag 10.

The bag main part or reservoir 12 is closed off tight, in particular liquid-tight, along its edges 20, 22 and along the first admission opening 24.

Arranged in the bag main part 12, there is an inner envelope 32 which, starting from the admission opening 24, extends in the longitudinal direction 28 of the bag main part 12 into the interior of said bag main part 12. The inner envelope 32 is open toward the admission opening 24, so that tissue introduced through the admission opening 24 first arrives in the interior of the inner envelope 32.

Like the envelope 14, the inner envelope 32 is formed from two foils 34 and 36 which lie flat on one another and are fixedly connected to one another at their edges 38 and 40, likewise by welding or heat-sealing, for example. The foils 34, 36 are transparent and are made of the same material as the bag main part 12, in the present case polyurethane. Alternatively, the inner envelope 32 can also be made of a material different than that of the bag main part 12, so that, because of their materials being matched to one another and because of their strength and thickness, the pairing of inner envelope 32 and bag main part 12 ensures particularly good sealing and a good fish trap effect, as will be described later.

Whereas the inner envelope 32 tightly closes off the bag main part 12 at the admission opening 24, the inner envelope 32 has a second opening 44 at an end 42 remote from the admission opening 24, so that tissue introduced through the admission opening 24 into the interior of the inner envelope 32 can be introduced through the admission opening 44 into the bag main part 12.

The end 42 of the inner envelope 32 is at a sufficient distance from an end 46 of the bag main part 12 lying remote from the admission opening 24.

The end 42 of the inner envelope 32 is generally spaced apart from the admission opening 24 by a distance which is in the region of approximately one quarter to approximately three quarters of the distance of the admission opening 24 from the end 46 of the bag main part 12 remote from the admission opening 24. In the illustrative embodiment shown, the end 42 of the inner envelope 32 is situated at about the halfway point in relation to the longitudinal direction 28 between the admission opening 24 and the end 46 of the bag main part 12.

The inner envelope 32 narrows in a funnel shape from the admission opening 24 to the admission opening 44, the end 42 of the inner envelope 32 being narrower, transverse to the longitudinal direction 28, than the bag main part 12 at the end 42 of the inner envelope 32. At the admission opening 24, the inner envelope 32 extends, transversely with respect to the longitudinal direction 28, across the full width of the extraction bag 10.

The inner envelope 32 is connected to the envelope 14 of the bag main part 12 only in the area of the admission opening 24, such that the inner envelope 32 is loose in relation to the envelope 14 of the bag main part 12, except in the area of the admission opening 24. In this way, the space between the outer face of the inner envelope 32 and the inner face of the envelope 14 in the area of the inner envelope 32 is also an inner space that can be used for accommodating tissue or fluid in the bag main part 12, or reservoir, which, as has already been mentioned, is closed off tight with respect to the admission opening 24, specifically by means of the inner envelope 32.

The inner envelope 32 is in particular integrally connected to the envelope 14 of the bag main part 12, i.e. the foils 16, 18 of the bag main part 12 and the foils 34, 36 of the inner envelope 32 are integrally joined or made in one piece with one another.

Figure 4:
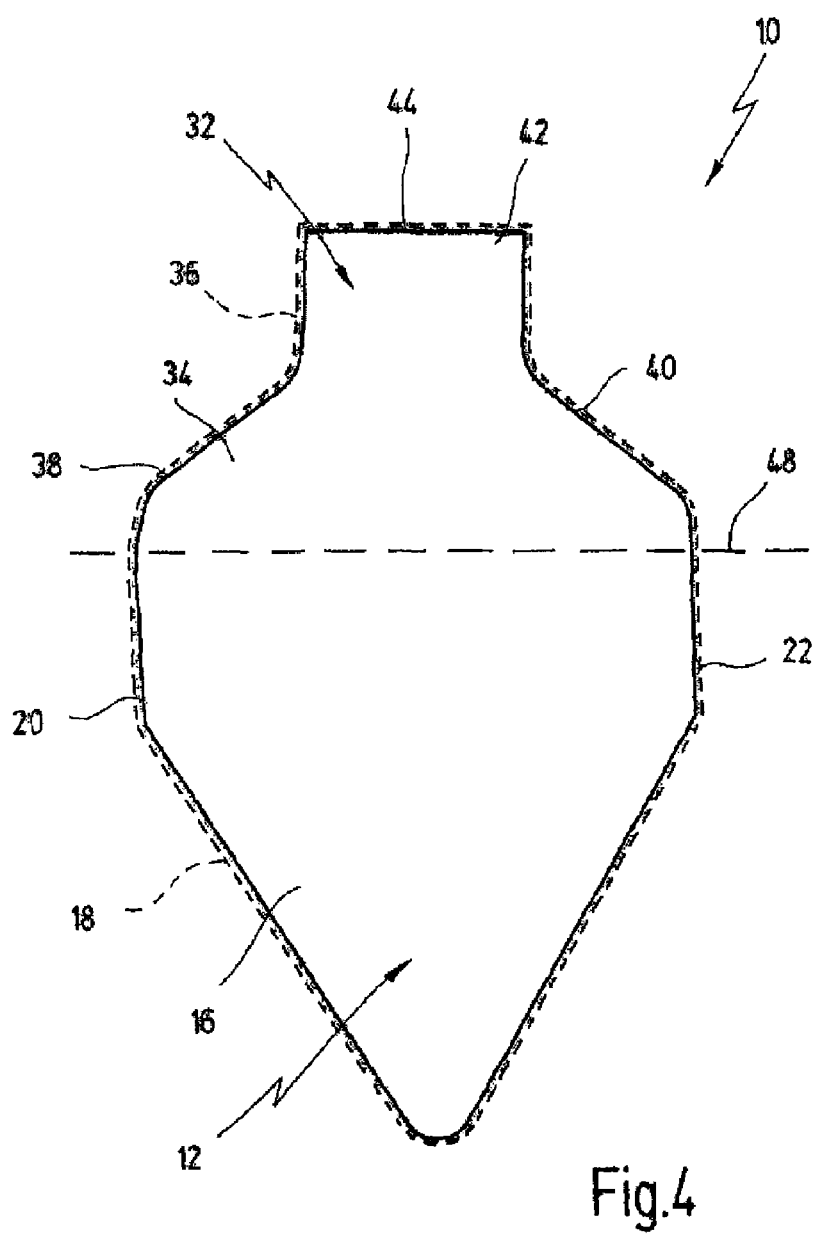
FIG. 4 shows the extraction bag from FIG. 1 at a previous production stage.

In FIG. 4, the extraction bag 10 is shown in an earlier stage of production.

The extraction bag is produced by means of two identical foil blanks being laid flat on one another and being connected fixedly and tightly to one another at the edges 20, 22 and 38, 40, except in the area of the admission opening 44, for example by welding or heat-sealing or adhesive binding. Alternatively, the starting form for the extraction bag could also already be a tubular shape with a closed end.

The blanks or the tubular starting form already have the later shape of the bag main part 12 and of the inner envelope 32, as is shown in FIG. 4.

In this way, the bag main part 12 and the inner envelope 32 are already present and joined together from the outset.

After the edges 20, 22, 38, 40 have been fixedly connected, the inner envelope 32 is then turned inward, approximately along a line 48, between the foils 16 and 18 of the bag main part 12, resulting in the extraction bag 10 with the inner envelope 32 according to FIG. 1.

Before the inner envelope 32 is turned inward into the bag main part 12, a thread loop 50 is placed between the foils 16, 18 and 34, 36, preferably before the edges 20, 22 and 38, 40 are fixedly connected to one another, such that the two free ends of the thread loop still to be connected to one another or a section of the already closed loop protrude outward after the edges 20, 22 and 38, 40 have been connected. In the alternative starting form for the extraction bag in the shape of a tube closed at one end, a passage for the thread loop would have to be created through the starting form for the extraction bag at a location lying on the side of the closed end of the starting form, viewed from the location where the extraction bag is intended to be turned inward. After the inner envelope 32 has been turned inward about the thread loop 50 and into the inside of the bag main part 12, the thread loop 50 then comes to lie in a pocket 52 which is delimited by a securing seam 54 that can be formed by heat-sealing or adhesive bonding. The securing seam 54 is applied after the inner envelope 32 has been turned inward, and it can additionally prevent the inner envelope 32 from being turned back out again from the bag main part 12.

The thread loop 50 allows the extraction bag 10 to be gripped by an instrument, for example forceps, and to this extent represents a means for gripping the extraction bag 10, and in particular it does not serve as a drawstring for closing the admission opening 24 as in the known extraction bags, because such a closure in the extraction bag 10 is in principle not needed for preventing escape of a tissue sample or fluid held in the bag main part 12.

Figure 5:
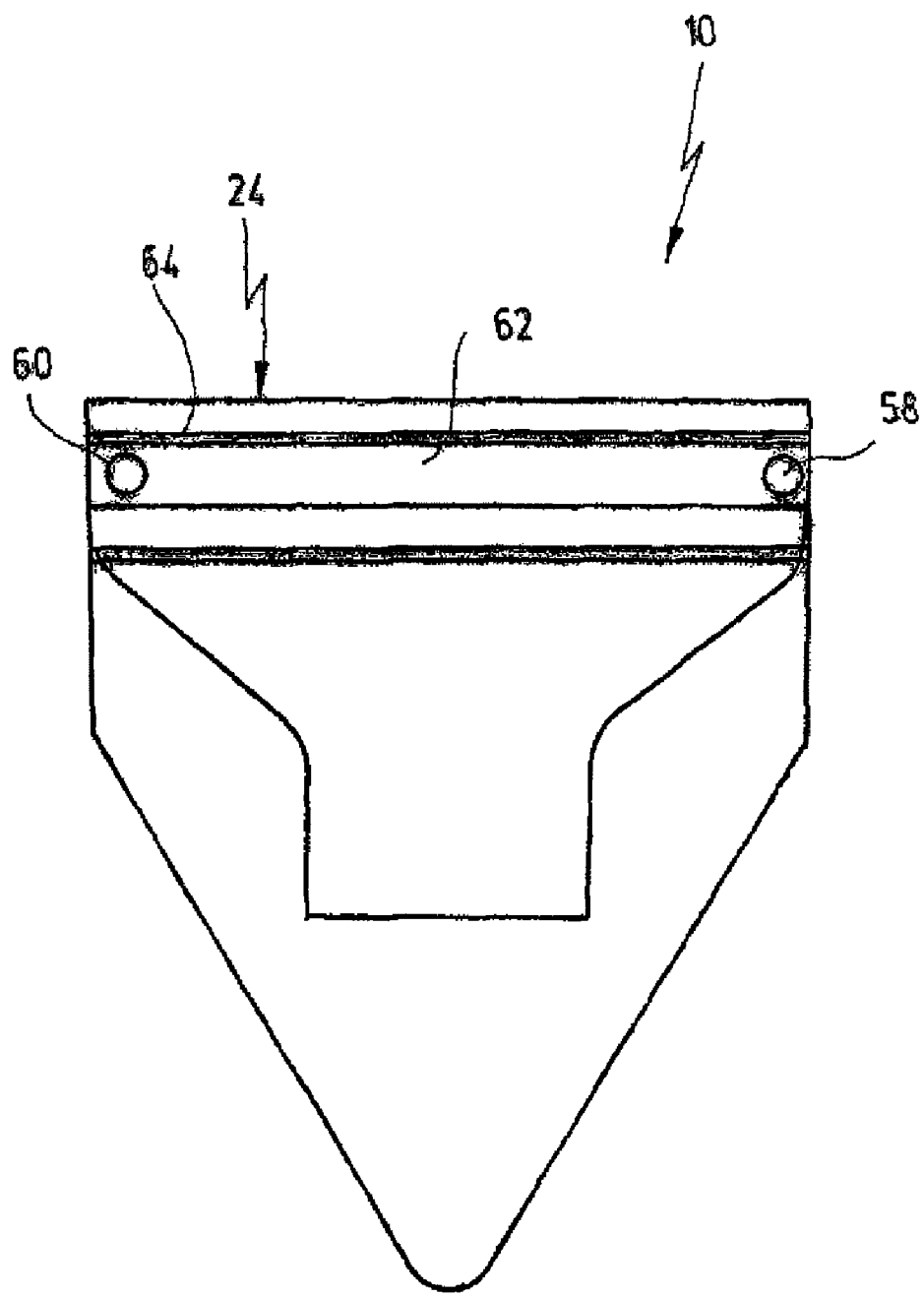
FIG. 5 shows a slightly modified illustrative embodiment of an extraction bag compared to the extraction bag in FIG. 1.

As an alternative or an addition to the thread loop 50, it is possible, according to FIG. 5, to also provide, as the means for gripping the extraction bag 10 in the body, an eyelet 58 or a further eyelet 60 which is/are applied on an envelope extension piece 62, such that the eyelets 58 and 60 do not impair the tightness of the bag main part 12. In particular, in the same way as was described for the illustrative embodiment with the thread loop 50, the envelope extension piece 62 can be tightly sealed by a securing seam on the closed side of the bag main part 12, seen from the eyelet 58 or the eyelets 58 and 60.

A closure means 64 for closing the admission opening 24 can also be provided on the envelope extension piece 62. Such a closure means 64 can, for example, be a zip closure of the kind known in bags used for food. As has already been mentioned, the closable nature of the admission opening 24 is not so much intended to prevent extracorporeal escape of tissue or fluid accommodated in the bag main part 12, but instead serves for example to prevent contaminants from getting into the bag main part 12 or reservoir, for example if the extraction bag 10 is stored for a certain period of time before removal of the tissue from the extraction bag 10, and also to avoid contamination of (healthy) body tissue by the tissue that is to be removed or the fluid that is to be removed.

Figure 6:
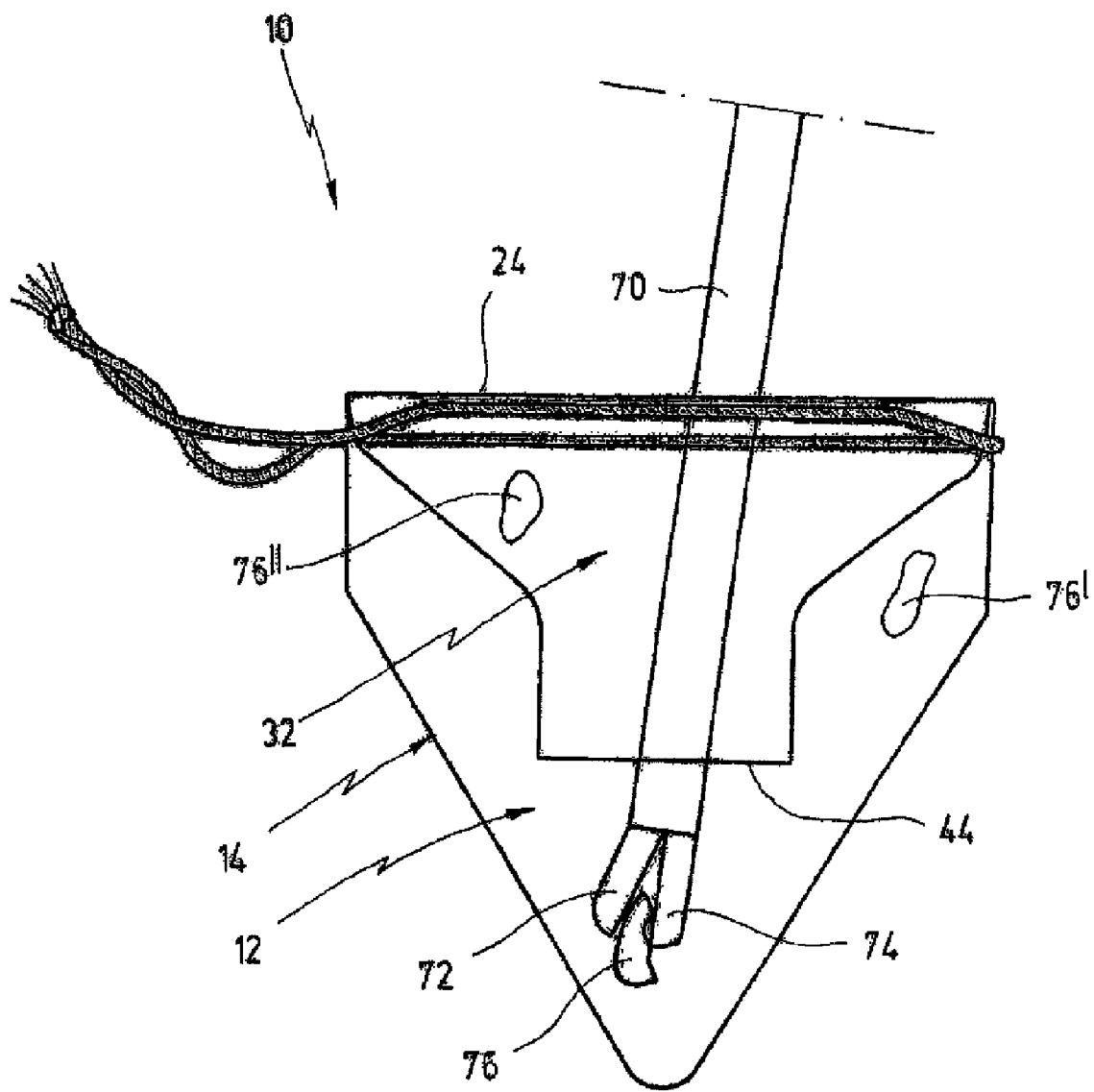
FIG. 6 shows a schematic representation of tissue being introduced into the extraction bag in FIG. 1.

Referring to FIG. 6, the introduction of body tissue or body fluid into the extraction bag 10 will now be described.

FIG. 6 is a schematic representation showing a distal area of an instrument 70 which, at the distal end, has jaw parts 72 and 74 with which a tissue piece 76 is gripped. To introduce the tissue piece 76 into the bag main part 12, the instrument 70 is guided, with the jaw parts 72, 74 to the front, through the admission opening 24, from there through the inside of the inner envelope 32 and then through the opening 44 of the inner envelope 32 and into the bag main part or reservoir 12. The tissue piece 76 is then released by opening the jaw parts 72, 74, and the instrument 70 is withdrawn from the extraction bag 10.

The inner envelope 32 now acts as a kind of valve with the function of a fish trap, i.e. tissue can be introduced through the opening 44 into the bag main part 12, but tissue, for example the tissue piece 76, cannot escape again from the bag main part 12, because said bag main part 12 is closed on all sides. The opening 44 itself forms only an extremely narrow gap or slit, because the inner envelope 32 is formed from two foils laid flat on one another, with the result that, even if the extraction bag 10 is held with the admission opening 24 facing downward, the tissue piece 76 cannot pass through the opening 44 again. The tissue piece 76 can still move to a position indicated by 76' or even to a position indicated by 76" when the extraction bag 10 is held with the admission opening 24 facing downward, but it cannot escape from the bag main part 12 because of the fact that said bag main part 12 is not open toward the admission opening 24. The position of the tissue piece 76 that is indicated by 76" is to be understood as signifying that in this case the tissue piece 76 is located between the outer face of the inner envelope 32 and the inner face of the envelope 14 of the bag main part 12.

Figure 7:
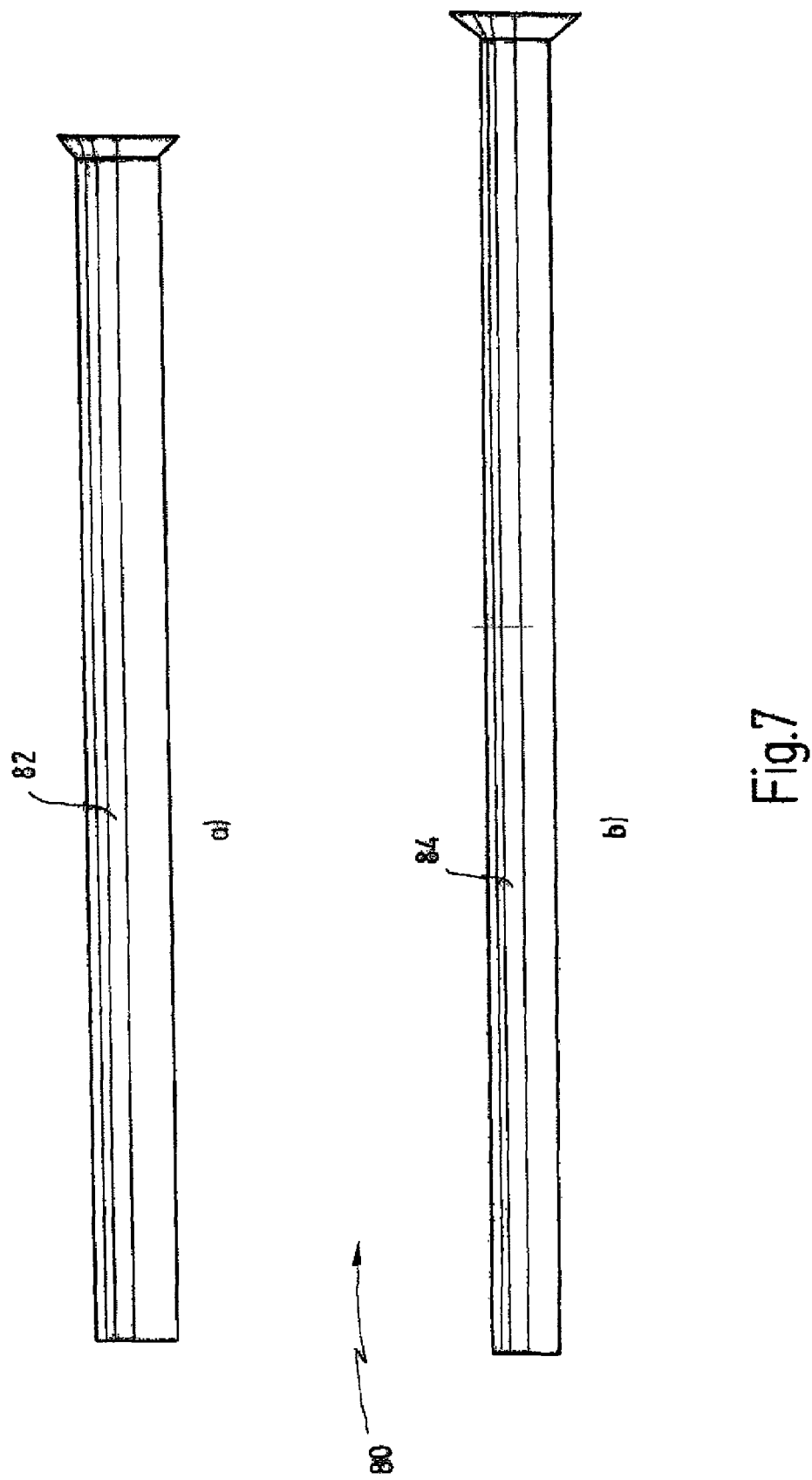
FIGS. 7a) and 7b) show an applicator for introducing an extraction bag into the body, FIG. 7a) showing a tube, and FIG. 7b) showing a ram component of the applicator.
Figure 8:
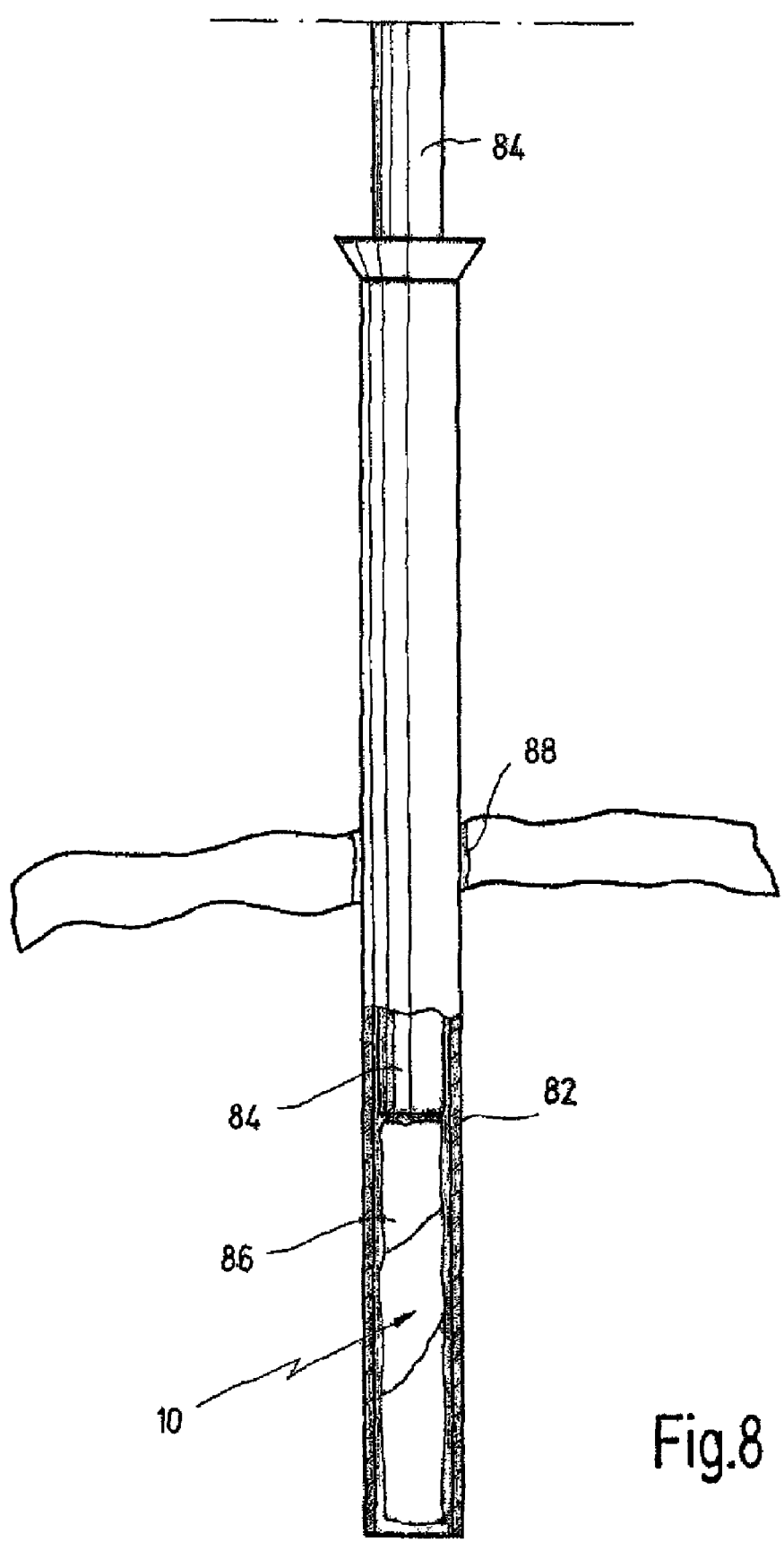
FIG. 8 shows the applicator from FIG. 7 during Its use for introducing an extraction bag into the body.

Referring to FIGS. 7 and 8, an applicator 80 is now described with which the extraction bag 10 can be introduced into the body.

The applicator 80 comprises a tube 82 of cylindrical shape, and a ram 84, likewise of cylindrical shape, which can be designed as a tube or rod, the external diameter of the ram 84 being adapted to the internal diameter of the tube 82 in such a way that the ram 84 can be inserted into the tube 82. The ram 84 is movable in the tube 82.

The extraction bag 10 can be rolled up parallel to the longitudinal direction 28, or transversely thereto, and in particular is designed in such a way that, from the rolled-up state, it converts more or less independently to an unrolled flat state when no external forces act on the extraction bag 10.

To apply or introduce the extraction bag 10 into the body, the extraction bag 10 is rolled up into a roll 86 as shown in FIG. 8. The roll 86 is then inserted into the tube 82, preferably from the direction of the distal end of the tube 82. The length of the tube 82 is adapted such that two rolls 86 of two extraction bags 10 can be received simultaneously one behind the other in the longitudinal direction of the tube 82.

The tube 82 is then introduced through a natural or artificially created opening 88 into the body, specifically to the site where the extraction bag 10 is needed to collect tissue.

The ram 84 is then inserted from the proximal direction into the tube 82, and, by pushing the ram 84 in the distal direction, the roll 86 is forced out from the distal end of the tube 82, and as soon as the roll 86 has completely emerged from the tube 82, the extraction bag 10 unrolls independently by virtue of its elastic properties.

Then, as shown in FIG. 6, tissue can be introduced into the extraction bag 10 in the manner described.

What is claimed is:

1. An endosurgical extraction bag for collecting body tissue or body fluid, comprising a bag main part formed from a flexible envelope, an inner envelope arranged in said bag main part, said inner envelope having: a first end connected to said bag main part and forming a first admission opening, but adjoining said bag main part sealingly in respect of said first admission opening, and a second end remote from said first admission opening and spaced apart from an end of said bag main part remote from said first admission opening which forms a second admission opening through which said tissue or fluid can be introduced into said bag main part;

wherein said inner envelope is integral with said envelope of said bag main part;

wherein said inner envelope is formed by turning inward of a section of said envelope of said bag main part;

wherein said extraction bag is sized and adapted for introduction into a body through a natural or artificial opening in said body; and wherein said extraction bag further comprises an eyelet to assist gripping said extraction bag by an instrument, wherein said eyelet is formed in the flexible envelope on an envelope extension piece between the first admission opening and the second admission opening.

2. The extraction bag of claim 1, wherein a space between an outer face of said inner envelope and an inner face of said envelope of said bag main part serves as a reservoir for said tissue or fluid.

3. The extraction bag of claim 1, wherein said inner envelope has a funnel-shaped configuration.

4. The extraction bag of claim 1, wherein said second end of said inner envelope is spaced apart from said first admission opening by a distance which is in the region of approximately one quarter to approximately three quarters of a distance of said first admission opening from said end of said bag main part remote from said first admission opening.

5. The extraction bag of claim 1, wherein said inner envelope is connected to said envelope of said bag main part only in its area directed toward said first admission opening.

6. The extraction bag of claim 1, wherein said second end of said inner envelope is narrower than said bag main part at said second end.

7. The extraction bag of claim 1, wherein said envelope of said bag main part is formed from two foils lying substantially flat on one another.

8. The extraction bag of claim 1, wherein said inner envelope is formed from two foils lying substantially flat on one another.

9. The extraction bag of claim 1, wherein said extraction bag is designed such that it can be rolled up and, from the rolled-up state, converts substantially automatically into an unrolled flat state.

* * * * *